United States Patent [19]
Mercer

[11] Patent Number: 4,952,594
[45] Date of Patent: * Aug. 28, 1990

[54] REAGENTS AND METHOD FOR THERAPEUTIC TREATMENT OF MULTIPLE SCLEROSIS

[76] Inventor: James B. Mercer, 13109 W. 95th St., Lenexa, Kans. 66215

[*] Notice: The portion of the term of this patent subsequent to Aug. 27, 2002 has been disclaimed.

[21] Appl. No.: 206,651

[22] Filed: Jun. 14, 1988

Related U.S. Application Data

[63] Continuation-in-part of Ser. No. 720,021, Apr. 19, 1985, Pat. No. 4,871,759, which is a continuation-in-part of Ser. No. 407,808, Aug. 13, 1982, Pat. No. 4,537,775, which is a continuation-in-part of Ser. No. 64,072, Aug. 6, 1979, Pat. No. 4,346,095, which is a continuation-in-part of Ser. No. 876,618, Feb. 10, 1978, Pat. No. 4,177,281, which is a continuation-in-part of Ser. No. 656,336, Feb. 9, 1976, Pat. No. 4,073,928, which is a continuation-in-part of Ser. No. 514,798, Oct. 15, 1974, Pat. No. 3,952,103, which is a continuation-in-part of Ser. No. 370,952, Jun. 18, 1973, Pat. No. 3,856,966.

[51] Int. Cl.$^5$ .................. A61K 31/415; A61K 31/52; A61K 31/425
[52] U.S. Cl. .................................. 514/398; 514/262; 514/368; 514/399
[58] Field of Search ........................................ 514/398

[56] References Cited

U.S. PATENT DOCUMENTS 4,537,775  8/1985  Mercer ................................ 514/398

OTHER PUBLICATIONS

Redfield, et al; Medical Intelligence, Disseminated Vaccinia in a Military Recruit with Human Immunodeficiency Virus (HIV) Disease; The New England Journal of Medicine, vol. 316, No. 11; 3/12/87.
Popko, et al; Myelin Deficient Mice: Expression of Myelin Basic Protein and Generation of Mice with Varying Levels of Myelin; Cell, vol. 48, 713–721; 2/27/87.
Wallis, Claudia; Probing a Mysterious "Cluster"; Time; 2/23/87.
Jacobs, et al; Multicentre Double-Blind Study of Effect of Intrathecally Administered Natural Human Fibroblast Interferon on Exacerbations of Multiple Sclerosis; The Lancet; 12/20–27/86.
Baum, Rudy M.; AIDS Researchers Make Inroads in Understanding a Complex Virus; C&EN; 12/1/86.
Klinman, et al; Effect of Cyclophosphamide Therapy on Oncogene Expression in Angioimmunoblastic Lymphadenopathy; The Lancet; 11/8/86.
Rosenberg, et al; A New Approach to the Adoptive Immunotherapy of Cancer with Tumor-Infiltrating Lymphocytes; Science, vol. 233; 9/19/86.
Stjernfeldt, et al; Maternal Smoking During Pregnancy and Risk of Childhood Cancer; The Lancet; 6/14/86.
Bailar III, et al; Progress Against Cancer; The New England Journal of Medicine; vol. 314, No. 19; 5/8/86.
Hardero, M.D., Jan Erik; An Association Between Cluster Headache and Herpes Simplex; The New England Journal of Medicine; 1/30/86.
Rosati, et al; Incidence of Multiple Sclerosis in Macomer, Sardinia, 1912–1981: Onset of the Disease After 1950; Neurology 36; 1/86.
Levy, et al; Cimetidine in the Treatment of Herpes Zoster; Journal of the Royal College of Physicians of London, vol. 19, No. 2; 4/85.
Straus, et al; Persisting Illness and Fatigue in Adults with Evidence of Epstein-Barr Virus Infection; Annals of Internal Medicine, vol. 102, No. 1; 1/85.
Jones, et al; Evidence for Active Epstein-Barr Virus Infection in Patients with Persistent, Unexplained Illnesses: Elevated Anti-Early Antigen Antibodies; Annals of Internal Medicine, vol. 102, No. 1; 1/85.
Product Information on Tagamet; Physician's Desk Reference; 1985.
Wakefield, Denis, M.B.B.S.; Cimetidine in Recurrent Genital Herpes Simplex Infection; Annals of Internal Medicine, vol. 101, No. 6; 12/84.
Shandira, Raymond, M.D.; Treatment of Herpes Zoster with Cimetidine; Canadian Medical Association Journal, vol. 131; 8/15/84.
Arnold, et al; Excessive Intracellular Acidosis of Skeletal Muscle on Exercise in a Patient with a Post-Viral Exhaustion/Fatigue Syndrome; The Lancet; 6/23/84.
Goldsmith, Marsha F.; Possible Herpesvirus Role in Abortion Studied; Jama, vol. 251, No. 23; 6/15/84.
Ashford, et al; Double-Blind Trial of Metronidazole in Malodorous Ulcerating Tumours; The Lancet; 6/2/84.
Shingles; The Harvard Medical School Health Letter, vol. IX, No. 8; 6/84.

(List continued on next page.)

Primary Examiner—Jerome D. Goldberg
Attorney, Agent, or Firm—Litman, McMahon & Brown

[57] ABSTRACT

The administration internally to humans of certain imidazol derivatives, especially 1-(Beta-hydroxyethyl)-2-methyl-5-nitro-imidazole (metgronidazole); N''-cyano-N-methyl-N'-[2[[(5-methyl-1H-imidazol-4-yl)methyl]thio]ethyl]-guanidine (cimetidine); 6-[1-methyl-4-nitro-imidazol-5-yl)thio] purine (azathioprine); L-(-)-2,3,5,6-Tetrahydro-6-phenyl-imidazo[2,1-b]thiazole (levamisole), or salts of the above compounds, is an effective therapeutic treatment for multiple sclerosis, both acute and chronic. The imidazole moeity is theorized to directly inhibit spread of the virus theorized to cause multiple sclerosis. Treatment of multiple sclerosis with metronidazole with one bolus dose on a frequency of once a day or less and with cimetidine on a frequency of twice per day has been found to be highly efficatious with minimal suppression of the patient's natural immune system and minimal long term peripheral nerve damage.

4 Claims, No Drawings

OTHER PUBLICATIONS

Oldstone, et al; Virus Persists in B Cells of Islets of Langerhans and is Associated with Chemical Manifestations of Diabetes; Science, vol. 224; 6/29/84.

Rebuck, et al; Cyclosporin in Pulmonary Sarcoidosis; The Lancet; 5/26/84.

Spiers, et al; Complete Remission in Hairy Cell Leukaemia Achieved with Pentostatin; The Lancet; 5/12/84.

Allison, et al; Cyclosporin for Crohn's Disease; The Lancet; 4/21/84.

Starzl, et al; Reversibility of Lymphomas and Lymphoproliferative Lesions Developing Under Cyclosporin-Steroid Therapy; The Lancet; 3/17/84.

Gunby, Phil; Viral Infection May Lead to Vessel Wall Problems; Jama, vol. 251, No. 9; 3/2/84.

Marwick, Charles; Nature of Autoimmune Disease Sought Through Treatment; Jama, vol. 251, No. 9; 3/2/84.

Bodansky, et al; Which Virus Causes the Initial Islet Lesion in Type I Diabetes?; The Lancet; 2/28/84.

Steinberg, Alfred D., M.D.; Cyclophosphamide—Should It be Used Daily, Monthly or Never?; The New England Journal of Medicine, vol. 310, No. 7; 2/16/84.

Mavligit, et al; Cimetidine for Herpes Zoster; The New England Journal of Medicine, vol. 310, No. 5; 2/2/84.

Pyke, et al; Reversibility of Diabetic Nephrophathy After Transplantation of Affected Kidney; The Lancet; 1/21/84.

Merion, et al; Cyclosporine: Five Years' Experience in Cadaveric Renal Transplantation; The New England Journal of Medicine, vol. 310, No. 3; 1/19/84.

Marklund, et al; The Effect of Tinidazole on Primary EBV Infection and Immunocompetence; Scand Journal Infect. Dis., 16:17-23; 1984.

Melbye, et al; Infectious Mononucleosis in Greenland: A Disease of the Non-indigenous Population; Scand Journal Infect. Dis., 16:9-15; 1984.

Hayne, et al; Herpes Zoster: Treatment with Cimetidine; Canadian Medical Association Journal, vol. 129; 12/15/83.

Cole, et al; Effects of Cyclosporine on Experimental Infections; Transplantation Proceedings, vol. XV, No. 4, Suppl. 1; 12/83.

Nussenblatt, et al; Treatment of Intraocular Inflammatory Disease with Cyclosporin A; The Lancet; 7/30/83.

Willebrand, et al; Cyclosporin-A Deposits in Renal Allografts; The Lancet; 7/23/83.

Davis, et al; Metronidazole Lowers Serum Lipids; Annals of Internal Medicine, vol. 99, No. 1; 7/83.

King, et al; Coxsackie-B-Virus-Specific IgM Responses in Children with Insulin-Dependent (Juvenile-Onset; Type I) Diabetes Mellitus; The Lancet; 6/25/83.

Stiller, et al; Cyclosporine for Treatment of Early Type I Diabetes: Preliminary Results; The New England Journal of Medicine, vol. 308, No. 20; 5/19/83.

Rockwell, et al; Inhibition of Delayed Hypersensitivity by Metronidazole and Misonidazole; Int. J. Radiation Oncology/Biology/Physics, vol. 9, No. 5; 5/83.

Treatment of Multiple Sclerosis; The Lancet; 4/23/83.

Lanza, et al; Malignant Neoplasms Occurring After Cardiac Transplantation; Jama, vol. 249, No. 13; 4/1/83.

Thornes, et al; Combination of Cimetidine with other Drugs for treatment of Cancer; The New England Journal of Medicine, vol. 308, No. 10; 3/10/83.

Miller, et al; Cimetidine and HDL Cholesterol; The Lancet; 3/5/83.

Srikanta, et al; Islet-Cell Antibodies and Beta-Cell Function in Monozygotic Triplets and Twins Initially Discordant for Type I Diabetes Mellitus; The New England Journal of Medicine, vol. 308, No. 6; 2/10/83.

Hill, et al; Interferon and Cimetidine for Malignant Melanoma; The New England Journal of Medicine; 2/3/83.

Hauser, et al; Intensive Immunosuppression in Progressive Multiple Sclerosis; The New England Journal of Medicine, vol. 308, No. 4; 1/27/83.

Laupacis, et al; Cyclosporin Prevents Diabetes in BB Wistar Rats; The Lancet; 1/1-8/83.

Roe, Francis J. C.; Toxicologic Evaluation of Metronidazole with Particular Reference to Carcinogenic, Mutagenic and Teratogenic Potential; Surgery, vol. 93, No. 1, Part 2; 1/83.

Urtasun, et al; Human Pharmacokinetics and Toxicity of High-dose Metronidazole Administered Orally and Intravenously; Surgery, vol. 93, No. 1, Part 2; 1/83.

Goldstein, Jay A., M.D.; Cimetidine and Mononucleosis; Annals of Internal Medicine, vol. 99, No. 3; 1983.

Aitcheson, et al; Frequency of Transforming Epstein-Barr Virus in Oropharyngeal Secretions of Rheumatoid Arthritis Patients; Intervirology 19:135-143; 1983.

Woyciechowska, et al; Multiple Sclerosis, Antiviral Antibodies; The Lancet; 12/25/82.

Freston, James W., M.D.; Cimetidine: Developments, Pharmacology and Efficacy, Annals of Internal Medicine, vol. 97, No. 4; 10/82.

Freston, James W., M.D.; Cimetidine: Adverse Reactions and Patterns of Use; Annals of Internal Medicine, vol. 97, No. 5; 11/82.

Corey, Lawrence, M.D.; The Diagnosis and Treatment of Genital Herpes; Jama, vol. 248, No. 9; 9/3/82.

Mertin, et al; Double-Blind Controlled Trial of Immunosuppression in the Treatment of Multiple Sclerosis: Final Report; The Lancet; 8/14/82.

Laupacis, M.D., et al; Cyclosporin A: A Powerful Immunosuppressant; CMA Journal, vol. 126; 5/1/82.

Melnick, et al; Isolation of Virus from the Spinal Fluid of Three Patients with Multiple Sclerosis and One with Amyotrophic Lateral Sclerosis; The Lancet; 4/10/82.

Adams, et al; Evaluation of Novel Radiation Sensitizers In Vitro and In Vivo; Radiation Oncology/Biology/Physics, vol. 8, No. 3 and 4; Mar.-Apr., 1982.

Clemmons, Lowell H., Sr., M.D.; Shingles, Herpes, Sex and Mononucleosis; Journal of the Medical Association of the State of Alabama; 3/82.

Pybus, P. K.: Metronidazole in Rheumatoid Arthritis; SA Medical Journal; 2/20/82.

Kurtzke, et al; Multiple Sclerosis in Iceland: 1. Evidence of a Postwar Epidemic; Neurology; 2/82.

Tobi, et al; Prolonged Atypical Illness Associated with Serological Evidence of Persistent Epstein-Barr Virus Infection; The Lancet; 1/9/82.

(List continued on next page.)

OTHER PUBLICATIONS

Davidson, et al; Treatment of Infectious Mononucleosis with Metronidazole in the Pediatric Age Group; Scand J. Infect. Dis. 14:103-104; 1982.

Gluckman, et al; Nephrotoxicity of Cyclosporin in Bone-Marrow Transplantations; The Lancet; 7/18/81.

Armerding, Dieter; Selective Induction of Immunological Tolerance in Antiviral T Killer Cells of Inbred Mice After Treatment with Cyclosporin A; Infection and Immunity; 6/81.

Braun, Peter, M.D.; Herpes Simplex Encephalitis; The New England Journal of Medicine; 5/14/81.

Lennard-Jones, J. E.; Azathioprine and 6-Mercaptopurine Have a Role in the Treatment of Crohn's Disease; Digestive Diseases and Sciences, vol. 26, No. 4; 4/81.

Keown, et al; Immunological and Pharmacological Monitoring in the Clinical Use of Cyclosporin A; The Lancet; 3/28/81.

Guinan, M.D., et al; The Course of Untreated Recurrent Genital Herpes Simplex Infection in 27 Women; The New England Journal of Medicine, vol. 304, No. 13; 3/26/81.

Whitley, M.D., et al; Herpes Simplex Encephalitis; The New England Journal of Medicine, vol. 304, No. 6; 2/5/81.

Woodland, et al; Azathioprine in Rheumatoid Arthritis: Double-blind Study of Full Versus Half Doses Versus Placebo; Annals of the Rheumatic Diseases; 1981.

Herreman, et al; Convulsive Seizures and Polyneuritis in a Patient with Lupus Treated with Metronidazole; Ann. Med. Interne; 1981.

Bunjes, et al; Cyclosporin A Mediates Immunosuppression of Primary Cytotoxic T Cell Responses by Impairing the Release of Interleukin 1 and Interleukin 2; Eur. J. Immunol.; 1981.

Crawford, et al; Studies on Long-Term T-Cell-Mediated Immunity to Epstein-Barr Virus in Immunosuppressed Renal Allograft Recipients; Int. J. Cancer; 1981.

Brincker, et al; Increased Breast-Cancer Recurrence Rate After Adjuvant Therapy with Levamisole; The Lancet; 10/18/80.

Stephenson, et al; Search for Canine-Distemper-Virus Antibodies in Multiple Sclerosis; The Lancet; 10/11/80.

Finegold, Sydney, M., M.D.; Metronidazole; Annals of Internal Medicine; 1980.

Spuy, et al; Cimetidine in the Treatment of Herpesvirus Infections; SA Medical Journal; 7/19/80.

Sander, M.D.; Hemorrhagic Endovasculitis and Hemorrhagic Villitis of the Placenta; Arch Pathol Lab Med, vol. 104; 7/80.

Vestergaard, et al; Type-Specific Herpes-Simplex--Virus Antibodies in Patients with Recurrent Duodenal Ulcer; The Lancet; 7/14/80.

Sleisenger, Marvin H., M.D.; How Should We Treat Crohn's Disease?; The New England Journal of Medicine; vol. 302, No. 18; 5/1/80.

Hedstrom, Sven Ake; Treatment of Anginose Infectious Mononucleosis with Metronidazole; Scand J. Infect. Dis.; 1980.

Kinlen, et al; Collaborative United Kingdom-Australasian Study of Cancer in Patients Treated with Immunosuppressive Drugs; British Medical Journal; 12/8/79.

Meredith, et al; Management of Cimetidine Overdose; The Lancet; 12/22-29/79.

Rustia, et al; Experimental Induction of Hepatomas, Mammary Tumors, and Other Tumors with Metronidazole in Noninbred Sas:MRC(WI)BR Rats; JNCI, vol. 63, No. 3; 9/79.

Minick, et al; Atheroarteriosclerosis Induced by Infection with a Herpesvirus; American Journal of Pathology, vol. 96, No. 3; 9/79.

van Rijhoven, A.W.A.M.; Cimetidine Intoxication; The Lancet; 8/18/79.

Ting, et al; Development of Donor-Specific B Lymphocyte Antibodies After Renal Transplantation; Transplantation; vol. 28, No. 1; 7/79.

Jeffrey, et al; Immunosuppression with Azathioprine, Prednisone and Cyclophosphamide; Transplantation, vol. 28, No. 1; 7/79.

Dodson, et al; Treatment of Infectious Mononucleosis with Metronidazole; Israeli Harefauh; 6/15/79.

Latt, Doreen; Cytotoxic Drugs in Rheumatoid Arthritis; The Medical Journal of Australia Special Supplement; 4/21/79.

Wilson, J. B.; Cymetidine Overdosage; Br. Medical Journal; 4/7/79.

Rosen, J. A.; Prolonged Azathioprine Treatment of NonRemitting Multiple Sclerosis; Journal of Neurology, Neurosurgery and Psychiatry; 1979.

Henle, et al; The Epstein-Barr Virus; Sc. Amer.; 1979.

Kasper, et al; Therapy of Crohn's Disease with Metronidazole-An Uncontrolled Trial; Acta Hepato-Gastroenterol; 1979.

Kurtzke, J. F., et al; Multiple Sclerosis in the Faron Islands, Ann. Neurol, vol. 5; 1979.

Uris May Induce Bowel Disease Relapses; Medical Tribune; 11/15/78.

O'Donoghue, et al; Double-Blind Withdrawal Trial of Azathioprine as Maintenance Treatment for Crohn's Disease; The Lancet; 11/4/78.

Hedstrom, et al; Treatment of Anginose Infectious Mononucleosis with Metronidazole; Scand J. Infect. Dis.; 7/9/78.

Warren, et al; Medical Intelligence, Isolation of Latent Herpes Simplex Virus from the Superior Cervical and Vagus Ganglions of Human Beings; The New England Journal of Medicine, vol. 298, No. 19; 5/11/78.

Morgan, Isabel; Metronidazone Treatment in Pregnancy; Int. J. Gynaecol. Obstet.; 1978.

Roe, J. F. C.; Metronidazole: Review of Uses and Toxicity; Journal of Antimicrobial Chemotherapy; 1977.

Symoens, J.; Control of Neoplasia by Modulation of the Immune System; Progress in Cancer Research and Therapy, vol. 2; 1977.

Levy, et al; A Blood Test for Multiple Sclerosis Based on the Adherence of Lymphocytes to Measles-Infected Cells; The New England Journal of Medicine, vol. 294, No. 26; 6/24/76.

(List continued on next page.)

OTHER PUBLICATIONS

Urtasun, et al; Radiation and High-dose Metronidazole in Supratentorial Glioblastomas; The New England Journal of Medicine, vol. 295; No. 25; 6/17/76.

Coddon, David R., M.D.; A New Viral-Hematologic Etiology Hypothesis for Chronic and Paroxysmal Headache Syndromes; Mount Sinai Journal of Medicine, vol. 41, No. 1; 1-2/74.

Rustia, et al; Induction of Lung... Lymphomas in Mice by Metronidazole; Journal of the National Cancer Institute; 1972.

Swannell, et al; Preliminary Results of Azathioprine Treatment in Severe Rheumatic Disease; Annals of Physical Medicine; vol. X, No. 3; 1969.

Taylor, Jo Ann T.; Pharmacodynamic Observations on Metronidazole Therapy. Side Effects in Endocrine, Metabolic and Auto-Immune Disorders. III—Anti-Ischemic and Anti-Flammatory Action...; Proc. of The Western Pharmocological Society of Washington Univ.; 1966.

Meulen, et al; The Possible Role of Viral Infections in Multiple Sclerosis and Other Related Demyelinating Diseases.

REAGENTS AND METHOD FOR THERAPEUTIC TREATMENT OF MULTIPLE SCLEROSIS

This is a Continuation-in-Part of U.S application Serial No. 720,021 filed Apr. 19, 1985, entitled METHOD OF TREATMENT OF MESENTERIC ADENITIS, now U.S. Pat. No. 4,871,759, which was a Continuation-in-Part of U.S. application Ser. No. 407,808 filed Aug. 13, 1982 entitled THERAPEUTIC TREATMENT FOR VIRAL INFECTIONS, now U.S. Pat. No. 4,537,775, which was a Continuation-in-Part of application Ser. No. 064,072, filed Aug. 6, 1979, now U.S. Pat. No. 4,346,095; which was a Continuation-in-Part of Ser. No. 876,618, filed Feb. 10, 1978, now Pat. No. 4,177,281; which was a Continuation-in-Part of Ser. No. 656,336, filed Feb. 9, 1976, now Pat. No. 4,073,928 which was a Continuation-in-Part of Ser. No. 514,798, filed Oct. 15, 1974, now U.S. Pat. No. 3,952,103; which was a Continuation-in-Part of Ser. No. 370,952, filed June 18, 1973, now U.S. Pat. No. 3,856,966.

BACKGROUND OF THE INVENTION

The invention herein described relates to an agent for, and a method of, treating progressive, nonremitting multiple sclerosis (hereinafter referred to as "multiple sclerosis"). In particular, this invention relates to the use of imidazole derivatives as general anti-viral agents.

Infectious agents, possibly viral in nature, together with an immune disorder, appear to cause multiple sclerosis. The following articles discuss theories relating to multiple sclerosis resulting from an infection, especially viral: Kurtzke, J. F., Hyllestad, K., *Multiple Sclerosis in the Faron Islands* Ann. Neurol 1979, Vol. 5, pages 6–21; Kurtzke, J. F., Gudmundson, K. R., Bergmann, S., *Multiple Sclerosis in Iceland: 1. Evidence of a Postwar Epidemic* Nour. 1982 Vol. 32, pages 143–50; Rosati, G., et al., *Incidence of Multiple Sclerosis in Macomber, Sardinia, 1912–1981: Onset of the Disease After 1950*, 14 Neurology 36, Jan. 1986.

Although it is not the intent of applicant to be bound herein to any particular theory or theories it is theorized by applicant and others that measles virus is the cause of multiple sclerosis. The following articles discuss this theory: Levy, N. L., Auerbach, P. S., Hayes, E. C., *A Blood Test for Multiple Sclerosis Based on the Adherence of Lymphocytes to Measles–Infected Cells*, N. Engl. J. Med. 294: 1424–27, 1976; Stevenson, J. R., Ter Meulen, V., Kisseling, W., *Search for Canine-Distemper Virus Antibodies in Multiple Sclerosis. A Detailed Variological Evaluation*, Lancet 2:772–75, 1980.

The measles virus genome appears to attack the susceptible gene of that particular chromosome that controls the production of myelin in central nervous system. This theory is discussed in Popko, B., Puckett, C., Lai, L., et al, *Myelin Deficient Mice: Expression of Myelin Basic Protein and Generation of Mice With Varying Levels of Myelin*, CEL 48:713–721, 1987.

In the past, treatments associated with multiple sclerosis have been ineffective for at least two reasons. There is substantial evidence that multiple sclerosis is virally caused and the significance of such evidence has not been recognized by the medical authorities. Thus, to date, no cure exists for multiple sclerosis because anti-viral agents have not been thought of as an appropriate drug for this virally induced disease. In addition, when more commonly used drugs with anti-viral properties, such as cyclophosphamide, are used to treat non-virally related symptoms or secondary, non-viral infections, their anti-viral efficacy in patients with viral infections has been masked by secondary complications which usually arise because of the drug's toxicity. Accordingly, there is disagreement concerning the value of cyclophosphamide in view of the harmful side effects. See, for example *Cyclophosphamide, Should It be Used Daily, Monthly, or Never?* New Engl. J. of Med., Vol. 310 No. 7, Feb. 16, 1984. There are, however, effective anti-viral agents with much lower levels of toxicity which would also be an effective treatment for multiple sclerosis as a virally induced disease.

While multiple sclerosis has been treated with medication, treatment has often been directed solely toward symptoms or secondary infections rather than to the viral cause. In general the medication has not been selective to the infecting virus and goes on to produce serious or even deadly secondary complications, especially suppression of the immune system. With the immune system depressed other infections and cancer eventually invade the patient and cause greater sickness or death.

Many of the imidazole derivative drugs described herein have been previously used in medicine for various purposes; however, their potential as broad anti-viral agents has not been generally recognized, apparently because each derivative typically has uses not directly related to any anti-viral activity. Thus, with the exception of 1-(Beta-hydroxyethyl)-2-methyl-5-nitro-imidazole (metronidazole), none of the substances described herein have been previously characterized as anti-viral agents. Metronidazole was so characterized by the present applicant in his U.S. Pat. No. 4,346,095.

The recognition of a general anti-viral agent began with metronidazole. Metronidazole is a known alkylating agent and derivative of imidazole. It appears that metronidazole can penetrate nearly all tissues of the body quite readily. Initially, it was erroneously believed that metronidazole was highly toxic and carcinogenic. This false belief delayed the recognition of metronidazole as a valuable anti-viral agent. Much of this error was probably due to the improper interpretation of certain medical data concerning the substance. It appears there were two basic sources of the false conclusions concerning metronidazole.

The first false conclusion was that metronidazole causes birth defects in children when given in the first trimester of pregnancy for the treatment of venereal trichomoniasis. While the literature does include several unsupported allegations concerning such a use of metronidazole, one study shows that, when metronidazole is given in all trimesters of pregnancy, the fetus in utero is actually protected from infectious agents. It is these infectious agents that are believed to cause many major and minor birth defects in the developing fetus; therefore, there may be fewer birth defects under metronidazole therapy. See, e.g., Morgan, I. F. K. "Metronidazole Treatment in Pregnancy", *Int. J. Obst. & Gyn.*, Vol. 15, p. 501 (1978). In the *Morgan* study, the untreated control group of pregnant women actually had more still births and congenital fetal malformations than the metronidazole treated mothers. Also, there has never been any epidemiologic evidence to support a conclusion that metronidazole causes birth defects in humans or rodents.

The second false conclusion was that metronidazole was carcinogenic. This allegation derived from studies on Swiss mice. See Rustia, M., Shibik, P. *Experimental*

*Induction of Hepatomas, Mammary Tumors and Other Tumors With Metronidazole in Noninbred Sas: WRC (WI) BR Rats*, JNCI, Vol. 63, p. 863 (1979) and *Induction of Lung . . . Lymphomas in Mice by Metronidazole;* JNCI, Vol. 48, p. 721 (1972). Rustia and Shubik were the principal proponents of the conclusion that metronidazole is carcinogenic. However, they apparently made several errors in arriving at this conclusion. First, they used unsuitable subjects, i.e. cancer-prone inbred animals. Second, they failed to recognize that the metronidazole fed Swiss mice significantly out-lived the controls. Since the metronidazole-fed rats outlived the controls and had fewer other diseases, a higher proportion of the metronidazole-fed animals would be expected to eventually develop cancer because they lived longer.

Applicant theorizes that the metronidazole prolonged the life of the subject species by suppressing viral infections until the immune system of the metronidazole-fed subject became depleted due to old age and could no longer prevent the natural onset of cancer or other diseases resulting from the failure of the immune system. Applicant specifically theorizes that the metronidazole was acting as an anti-viral agent and was controlling viral infection in the test subjects. With these viral infections controlled, the test species lived longer. Thus, metronidazole cannot be concluded as carcinogenic on the basis of this data.

Tests were conducted using metronidazole on humans for the treatment of viral related disorders. The metronidazole proved to be very beneficial in relieving such disorders. Details of these trials are discussed in the parent applications which are incorporated herein by reference and by the detailed description of the present application.

Metronidazole is a substituted imidazole of the formula $C_6H_9N_3O_3$. It has the following structure:

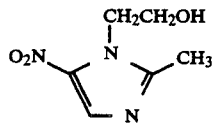

Metronidazole is theorized to interfere with nucleic acid biosynthesis and it is further theorized that its effectiveness in the treatment of viral infections relates to blockage or interference with the viral metabolism cycle necessary for cell infection. It appears likely that metronidazole acts by suppressing viral production while natural body defenses function to eliminate viral material from the system, although it is not the intent of applicant to be confined to this theory or, as noted before, the other theories presented herein.

Applicant has studied other compounds possessing a similar structure, the appropriate bioavailability and suitable non-fatal toxicological and carcinogenic properties as useful anti-viral agents. Applicant theoretically determined that the imidazole moiety of metronidazole was the active part of the compound. Therefore, it is postulated that other imidozole compounds, including N'''-cyano-N-methyl-N'-[2[[(5-methyl-1H-imidazol-4-yl)methyl]thio]-ethyl]-guanidine (cimetidine), 6-[1-methyl-4-nitroimidazol-5-yl) thio]purine (azathioprine) and L-(-)-2,3,5,6-Tetrahydro-6-phenyl-imidazo [2,1-b]thiazole (levamisole), would also be broad anti-viral agents. In many instances the acid salt of the compound would be the actual drug administered; however, no distinction will be made between the substance and its salts herein.

Cimetidine is one of the most widely used drugs in the world. Its primary use has been in the treatment of gastritis, since it apparently markedly reduces the volume and concentration of acid secreted, both in the resting state and after stimulation by food, histamine, pentagestrin, insulin and caffeine. Despite its wide use in certain areas of medicine, cimetidine is not recognized as a nearly universal anti-viral agent.

In 1977, Van Der Spuy, Levy and Levin treated a woman having a gastric ulcer with cimetidine. The woman was also suffering from Herpes zoster at the time and under the cimetidine treatment she appeared to obtain relief from the herpetic pain. This led to a postulation that cimetidine might be useful in the treatment of herpes zoster infections. Further studies tended to support this hypothesis. For example see S. Van Der Spuy, D. W. Levy, W. Levin, *Cimetidine in the Treatment of Herpes Virus Infections*, SA Mediese Tydskrif, p. 112, 19 July 1980. However, while cimetidine was postulated by Levy et al. as a possible agent for treatment of herpes zoster, it was not recognized as a potentially universal, or nearly universal, anti-viral agent.

In addition, cimetidine may be too toxic for use in human immunal deficiency virus infected patients due to a tendency to cause blood dyscrasias.

Cimetidine has the formula $C_{10}H_{16}N_6S$ and exhibits the following chemical structure:

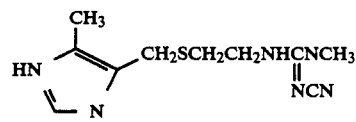

Thus, it is a substituted imidazole.

Azathioprine has the formula $C_9H_7N_7O_2S$ and exhibits the following structure:

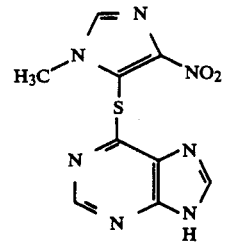

It is, therefore, also a substituted imidazole. Clinically, azathioprine is known to decrease the number of mononuclear and granulocytic cells available for migration to an area of inflammation. It is also known to inhibit the proliferation of promyelocytes within bone marrow, thus decreasing the number of circulating monocytes available to become macrophages in the peripheral blood. Its primary use has been as an anti-inflammatory agent for the prevention of rejection in renal homotransplantation. It has also been used for systemic lupus erythematosus, rheumatoid arthritis, polymyositis and Crohn's disease. It is not recognized as a general anti-viral agent.

Levamisole has the formula $C_{11}H_{12}N_2S$ and exhibits the following chemical structure:

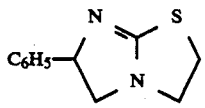

It is a partially reduced, multiply substituted, imidazole. Levamisole is observed to stimulate parasympathetic and sympathetic ganglia, as do certain antidepressant drugs, and it possesses some mood elevating activity. It also has time- and dose-dependent regulatory characteristics that enhance or inhibit immune responses to a variety of antigens. It has not, however, been recognized as an agent likely to inhibit viral development and thus possess anti-viral characteristics.

Applicant theorizes that, especially with metronidazole, fewer side effects, such as peripheral nerve damage sometimes associated with frequent doses of metronidazole, will result, if given in large infrequent doses (daily or less often) rather than in smaller multiple daily dosages. Single daily oral bolus doses give an effective lytic metronidazole dose and avoids the complicating peripheral neuropathy syndrome in patients with good kidneys.

Further, applicant theorizes that metronidazole is substantially less harmful than the other two imidazole derivatives (cimetidine and azathioprine) and is also substantially less harmful than cyclophosphormide, the anti-viral and chemotherapeutic agent in use for more than thirty years. The other three agents, unlike metronidazole, while effective in combating virus infections, also cause substantial damage to the immune system.

OBJECTS OF THE INVENTION

The objects of this invention are: to provide a class of substances for systematically treating multiple sclerosis; to provide a method of treating multiple sclerosis with these substances; to provide such a method that is suitable for intensive therapy as well as long-term maintenance and intermittent therapy; to provide such a method including the application of bolus doses of the substances at periods of one day or more to avoid complications; and to provide such a treatment which is easily administered with few or no complications and which is also usually well tolerated by the recipient.

Other objects and advantages of this invention will become apparent from the following descriptions and examples wherein are set forth, by way of illustration and example, certain embodiments of this invention.

SUMMARY OF THE INVENTION

Anti-viral agents are provided for treatment of viral and viral-related disorders, especially multiple sclerosis. These agents belong to a group of compounds which are derivatives of imidazole. It is theorized that the imidazole moiety acts directly to inhibit spread of a virus theorized to be the cause or theorized to combine with other unknown factors to be the cause of multiple sclerosis.

While it is believed that any non-toxic, pharmaceutically acceptable substituted imidazole of sufficient bioavailability may be administered according to the present invention, four specific examples are provided. These are 1-(B-hydroxyethyl)-2-methyl-5-nitroimidazole (metronidazole); N'''-cyano-N-methyl-N'-[2[[(5-methyl-1H-imidazol-4-yl) methyl]thio]-ethyl]-guanidine (cimetidine); 6-[1-methyl-4-nitro-imidazol-5-yl)thio]purine (azathioprine); and L-(-)-2,3,5,6-Tetrahydro-6-phenylimidazo[2,1-b]thiazole (levamisole). These compounds, or their acid salts, are believed to be particularly well suited for the medical applications.

While it is believed that each of the imidazoles is an effective anti-viral agent, metronidazole and cimetidine have been found to be generally free of severe side effects. In particular, levamisole and azathioprine are effective as anti-viral agents, but must be used in extremely low doses with an attendant reduction in the efficacy thereof.

In particular, it is theorized that levamisole, and to a lesser extent azathioprine are strong immune system suppressants. If each is used in sufficient quantities to control the virus then the immune system is depressed to a point where diseases and cancer become prevalent and potentially life threatening. This same effect is seen in cyclophosphamide which is well recognized as being antiviral, but which also suppresses the immune system allowing other virally and bacterially induced diseases, and especially cancer, to invade the patient's system and eventually lead to severe illness or death.

It is theorized that multiple sclerosis is caused by a measles virus present in genetically susceptible patients. For such patients, it is further theorized that the measles virus causing multiple sclerosis may be inherited. In genetically susceptible patients, a healthy immune system continuously attacks and maintains the presence of the virus in the hosts at such low levels that the virus is effectively dormant. It is only when the immune system of such patients is sufficiently compromised that the measles virus reproduce at a rate that exceeds the compromised immune system's ability to effectively respond. Under such circumstances, the virus appears to become activated and the symptoms of multiple sclerosis are manifested in the patient. The immune system, in genetically susceptible patients, can be compromised for any number of reasons, including other incidental virally induced diseases, extreme emotional or physical stress, and in female patients, from the immune system responses to pregnancy.

The administration of effective anti-viral amounts of pharmaceutically acceptable compositions comprising a substituted imidazole operates to compensate for the compromised and debilitated immune system by operating to kill the virus responsible for multiple sclerosis to such an extent that the symptoms of multiple sclerosis will not be manifested. Further, the drug's adverse effects on an already weakened immune system can be minimized if the imidazole used for treatment of multiple sclerosis is metronidazole.

It is foreseen that a maintained dosage of the imidazole will be required virtually for the life of the treated patient to prevent the multiple sclerosis virus from again becoming active and causing reoccurring symptoms.

It is theorized that almost any virus may be controlled to some extent with the imidazole compounds of the present invention. It is thus foreseen that the treatment disclosed herein may be effective for diseases theorized to be virally induced, including: autosomal dominant genetic disease, polycystic renal disease, insulin dependent diabetes mellitus, hereditary breast cancer, Huntington's disease, Duchenne muscular dystrophies, and auto-immune deficiency syndrome (AIDS). In particular, it is contended that multiple sclerosis may be effectively treated with imidazoles and derivatives thereof.

While administration of a large initial concentration of the therapeutic agent followed by a tapering off of concentration throughout the day has been found to be highly effective in treating the virus, certain of the imidazoles cause some peripheral nerve damage, as identified by tingling of the skin or the like. Applicant has found that a single daily or less frequent large dose of the agent rather than multiple small doses are less likely to result in such nerve damage, especially when the imidazole is metronidazole.

As noted above, it is theorized that the imidazole moiety acts by suppressing viral production while natural body defenses function to eliminate the virus from the system. It is also theorized that the effectiveness of the imidazole derivatives relates to their ability to block or interfere with the viral metabolism cycle. However, many years of careful experimentation will be necessary to prove or disprove these theories and it is not the intent of the applicant to be confined to them for purposes of this application.

DETAILED DESCRIPTION AND EXAMPLES

As required, detailed embodiments of the present invention are disclosed herein; however, it is to be understood that the disclosed embodiments are merely exemplary of the invention which may be embodied in various forms. Therefore, specific details disclosed herein are not to be interpreted as limiting, but merely as a basis for the claims and as a representative basis for teaching one skilled in the art to variously employ the present invention in virtually any appropriately detailed structure.

Imidazole derivatives of sufficient bioavailability are theorized to be effective antiviral agents. Bioavailability refers to the ability of the drug to move through the involved biological system to the active site at which it can act upon the virus.

Of course, practical application of these imidazole drugs requires that the moiety, or substituted moiety, be part of a pharmaceutically acceptable compound. That is, the compound must not exhibit significant toxic effects at its therapeutic levels and it should not be appreciably carcinogenic. Therefore, the only significant limitations on drugs having the substituted imidazole moiety for use according to the present invention are pharmaceutical acceptability and bioavailability. Metronidazole, cimetidine, azathioprine, and levamisole are drugs which include the imidazole moiety, have the appropriate bioavailability and are sufficiently low in toxicity to be effective as antiviral agents. In levamisole, the imidazole moiety has been partially reduced. Specific examples and hypotheticals describing treatment with these drugs, or their acid salts, of multiple sclerosis are presented below.

The preferred treatment process involves administration of the anti-viral agent in large relatively infrequent dosages, once a day or less frequently with metronidazole and other imidazoles having relatively long half lives within the patient. With cimetidine and other imidazoles having relatively short half lives, more frequent doses are necessary; for example, two doses per day for cimetidine. The dosage depends on body weight and the imidazole utilized. For metronidazole a preferred dosage is about 500 milligrams of metronidazole in a suitable pharmaceutical carrier taken once per day per 155 pounds of body weight, however, a range of from approximately 30 mg to 2,500 mg on the average per 24 hour period may be administered in accordance with the invention. The dosage may be substantially reduced following initial administration over a period including a plurality of months. A preferred method of administration of metronidazole is to administer to the host 20 mg of metronidazole per kilogram body weight for approximately every 24 hours in a single oral dosage. For cimetidine, doses of 1200 to 2000 milligrams per day as tolerated in patients given on a frequency of twice per day have been effective. During treatment for active symptoms, the dosage may be greater than for maintenance once the active symptoms caused by the virus have stopped. A large dose once a day or the like will permit the inducement of a high concentration of the agent in the biological system for a short period of time followed by a tapering off of the concentration. This should lead to effective treatment while at the same time avoiding toxicity problems and side effects.

While the above described treatment has been directed to humans having multiple sclerosis, it is foreseen that the treatment method may be applicable to a wide variety of virally induced or enhanced diseases. In particular, it is foreseen that metronidazole may be used to treat rubella, Huntington's Chorea, varicella, cytomegalovirus, allergic encephalomyelitis, azoospermia, Type A viral influenza, viral thyroiditis, carpal tunnel syndrome, viral psoriasis, viral amyotrophic lateral sclerosis, macular degeneration of the retina, viral diverticulitis, infectious mononucleosis, rheumatoid arthritis, juvenile rheumatoid arthritis, Granulomatosis, ateriosclerosis, ulcers of the feet, Herpes simplex 1, Herpes simplex 2, Herpes zoster, duodenal ulcer disease, Herpes labialis and Herpes keratitis. It is also foreseen that the treatment method may be applicable to scrapie in sheep.

The following examples are presented for the purpose of illustrating the efficacy of the methods of the present invention and are not intended to be a limitation of the scope of the present invention.

EXAMPLE 1

A twenty-four year old white female developed muscular weakness on the left side of her body following the birth of her second child. The onset of the muscular weakness was accompanied by disturbed sensory changes in the affected side of her body. It appeared that she had contracted an incidental viral infection. The condition worsened with the onset of severe mood fluctuations and chronic fatigue unrelieved by rest. These symptoms were characteristic of a typical patient having multiple sclerosis. The condition was complicated by a pelvic congestion syndrome. The latter problem was cured with surgery after which she was given a trial dose of metronidazole, 250 milligrams (hereinafter mg), b.i.d. for seven weeks. Following her discharge from the hospital she received 500 mg per day of metronidazole for six weeks. Her grip strength on a hand dynomometer increased significantly. As the dosage was increased her hand strength increased as measured by the dynomometer. The dose was increased to 500 mg, once every eight hours for six weeks. At the end of this period her hand strength increased again by about forty percent. The dosage was tapered off over the next four weeks and then stopped.

Since the termination of the metronidazole therapy she has continued to work outside the home and has had no relapses to date.

EXAMPLE 2

A forty-two year old white male who weighed 240 pounds experienced paralysis on the left side of his body as he was working on his farm. This condition resulted in an absence of strength in the left upper and lower extremeties. His condition was diagnosed as multiple sclerosis. A 500 mg daily dosage of metronidazole was administered. Following six months of metronidazole therapy, his hand strength increased by about one hundred and ten percent. At that time, his strength was regained sufficiently to resume work activities. The symptoms did not recur while maintaining this dosage. After about one year the patient, on his own initiative, stopped the dosage. The symptoms returned but with other complications, such as thrombophelibitis. The patient was thereafter placed on an oral bolus dose of from 2000 to 2500 milligrams per day for two years Thereafter, treatment was stopped and no relapse to date.

EXAMPLE 3

A fifteen year old woman was hospitalized following uncontrolled vomiting, after which she experienced the onset of severe headaches and great fatigue. She was tentatively diagnosed as having multiple sclerosis. She was started on metronidazole, 250 mg daily. Following the administration of metronidazole her headaches and paralysis were eliminated. However, over the next four years the problems would return as she would stop taking the metronidazole. Some years later following a pregnancy and during a period of her life when she was not taking metronidazole she developed neurological symptoms consistent with active multiple sclerosis. She ultimately resumed the administration of metronidazole at a higher dosage of 750 mg daily, for eight weeks. The symptoms subsided immediately with no relapse to date.

EXAMPLE 4

A thirty year old white female developed chronic fatigue following the birth of her first child. Following the birth of her second child her chronic fatigue worsened and she developed severe headaches. Eight years following the birth of her first child she developed a tendency to fall easily, began experiencing dizzy spells, and experienced a loss of hand strength. Subsequently she became pregnant and because of the potential danger posed by pregnancy to a person experiencing these symptoms, the pregnancy was aborted. Following an abortion her condition worsened and a diagnosis revealed multiple sclerosis. She was placed on a 500 mg dose of metronidazole daily. However, although her condition improved with the administration of this drug, she would frequently forget to take it and her condition would worsen. Her dose was increased to 2,000 mg daily for two months. At this high dosage rate a chronic neurotoxicity with nightmares and severe depression was controlled with prochlorperazine, 15 mg spansule b.i.d. Following the 2,000 mg daily dose administration the disease went into remission and without relapse to date.

EXAMPLE 5

A thirty-one year old female became ill with symptoms of London viral influenza. These symptoms were accompanied by heaviness and weakness in the right side of her body. Later that year she was diagnosed with multiple sclerosis. Within a year of the diagnosis she had contracted acute viral thyroiditis. Within the following year she was hospitalized with a gastric ulcer and with symptoms of gall bladder disease and epigastric pain. Surgery was performed to remove a massive penetrating gastric ulcer involving the pancreas, producing pancreatitis. Following an antrectomy, she suffered bilateral pneumonia from aspiration of gastric contents. Following recovery from the surgery, she was in a very weakened state dragging her left foot when walking. She was administered 1,500 mg of metronidazole daily for two weeks. Thereafter the dosage rate was increased to 2,000 mg daily for about two weeks. Following about four weeks of high dose metronidazole therapy the disease went into remission.

The symptoms did not relapse for seven years, at which time, because of the administration of corticosteroids (prednisone) for breathing difficulties, it is theorized, dormant viruses in her body were activated which lead to her death.

EXAMPLE 6

A fifty-five year old white female was struck by paralytic polio earlier in her life. The disease involved the right side of her body, primarily the right upper and lower extremities, leaving her with a handicap due to the lack of strength in the right lower extremity. Prior to June, 1976, she successfully gave birth to three children. Then on June 18, 1976, she experienced numbness in the left side of her face with some loss of sensation that involved the left fifth cranial nerve and the left eighth cranial nerve that accounts for symptoms of verdigo. There was also evidence of ninth and tenth left cranial nerve loss due to lack of gag reflex. Involvement of the left lower extremity was manifested by a tendency to stagger to the left and also by a poor tandem walking ability. She also had 1+ bylateral Babinski reflexes and experienced hemiparesis of the right hand and foot. Over the next four years the symptoms culminated with the individual inadvertently dropping objects and bumping into walls. She experienced lapses of memory and a failure to fully comprehend the activities in her surrounding environment. She was started on metronidazole, 250 mg, q.i.d., which occasionally had to be lessened due to nausea. She was maintained on this general dosage level for six months at which time the above noted symptoms cleared and have not to date returned.

It is to be understood that while certain forms of the present invention have been illustrated and described herein, it is not to be limited to the specific forms or arrangement of parts described and shown.

What is claimed and desired to be secured by Letters Patent is as follows:

1. A method for treating a human host having multiple sclerosis comprising repeatedly orally administering a dosage of a composition including metronidazole to a human host in need of said treatment, said dosage including metronidazole in a range from approximately 30 mg to 2500 mg on the average per 24 hour period.

2. The method of claim 1 wherein said dosage is substantially reduced following initial administration over a period including a plurality of months.

3. A method according to claim 1 wherein said dosage is about 20 milligrams of metronidazole per kilogram body weight per day.

4. A method according to claim 3 wherein said dosage is given in an effectively single oral administration of approximately 20 milligrams of metronidazole per kilogram body weight approximately every 24 hours.

* * * * *